United States Patent [19]

Edwards et al.

[11] Patent Number: 4,546,202

[45] Date of Patent: Oct. 8, 1985

[54] PROCESS FOR THE RECOVERY OF COBALT AND MANGANESE FROM OXIDATION RESIDUE INCINERATOR ASH, PYROLYSIS SAND AND PYROLYSIS CHAR

[75] Inventors: Robert C. Edwards, Naperville, Ill.; F. Austin Golson, Decatur, Ala.

[73] Assignee: Amoco Corporation, Chicago, Ill.

[21] Appl. No.: 555,935

[22] Filed: Nov. 29, 1983

[51] Int. Cl.$^4$ ............................................. C07C 51/265
[52] U.S. Cl. .................... 562/414; 260/429 R; 260/439 R; 502/22; 502/28; 556/49; 556/149
[58] Field of Search .................. 562/414; 260/439 R, 260/429 R; 502/22, 28

[56] References Cited

U.S. PATENT DOCUMENTS

| | | | |
|---|---|---|---|
| 2,157,767 | 5/1939 | Long | 260/439 R |
| 2,833,816 | 5/1958 | Saffer et al. | 562/416 |
| 2,964,559 | 12/1960 | Burney et al. | 260/429 R |
| 3,133,942 | 5/1964 | Hahl | 260/429 R |
| 3,341,470 | 9/1967 | Hensley | 562/414 |
| 3,776,930 | 12/1973 | Wu | 260/439 R X |
| 4,060,535 | 11/1977 | Cinco | 260/439 R X |
| 4,258,227 | 3/1981 | Allen et al. | 562/479 X |
| 4,266,084 | 5/1981 | Allen | 260/464 X |
| 4,393,264 | 7/1983 | Allen | 585/469 |
| 4,417,972 | 11/1983 | Francis et al. | 502/22 X |

Primary Examiner—Natalie Trousof
Assistant Examiner—Patricia M. Scott
Attorney, Agent, or Firm—Gunar J. Blumberg; William T. McClain; William H. Magidson

[57] ABSTRACT

A process for the recovery of cobalt and manganese from solid aromatic acid oxidation incinerator ash, pyrolysis sand and pyrolysis char is disclosed. The process comprises heating the solid residue at a temperature of about 120° to about 300° C. and a pressure of about 3 atmospheres to about 30 atmospheres. The recovered catalyst is useful for the oxidation of alkyl aromatic hydrocarbons to their corresponding di- or tricarboxylic acids which are used for the manufacture of fibers, films and molded products.

2 Claims, No Drawings

PROCESS FOR THE RECOVERY OF COBALT AND MANGANESE FROM OXIDATION RESIDUE INCINERATOR ASH, PYROLYSIS SAND AND PYROLYSIS CHAR

FIELD OF THE INVENTION

The field of this invention relates to the recovery of cobalt and manganese in the form of their acetate salts directly from a mixed metal oxide in incinerator ash, pyrolysis sand or pyrolysis char.

BACKGROUND OF THE INVENTION

In the commercial manufacture of benzene di- or tricarboxylic acids (e.g., isophthalic acid [IPA], terephthalic acid [TA] or trimellitic acid [TMLA]), a residue is obtained (after maximizing recovery of such acid and recovery for reuse of the reaction solvent), which is a mixture of oxygen-containing derivatives of benzene and toluene which are mono-, di- and tricarboxylic acids, aldehydocarboxylic acids, and methylol-substituted benzene or toluene or their carboxylic (benzoic or toluic) acids and which also contains components of catalysis. Usually such components of catalysis are Co-Mn-Br or Co-Mn-Ce-Br from liquid phase oxidation of a xylene or pseudocumene (1,2,4-trimethylbenzene) with air in the presence of acetic acid reaction solvent. A similar residue is also obtained from the neat oxidation of liquid o-xylene with air in the presence of Co-Mn-Br catalyst system after dehydrating the o-phthalic acid formed to its anhydride under conditions which vaporize the anhydride, water and materials boiling between the anhydride and water. While such residues amount to from 2 to 25 weight percent of the benzene di- or tricarboxylic acid produced, such residue production annually is substantial in view of the millions of kilograms of the benzene di- or tricarboxylic acids produced annually.

Such residues contain water-soluble benzene carboxylic acids and water-soluble forms of the components of catalysis. Landfill disposal of such residues is undesirable because rain and groundwater leach out those carboxylic acids and soluble forms of the components of catalysis and can contaminate surface run-off water and eventually streams as well as below-surface aquifers. Disposal of the organic residues can be made by the processes as disclosed in U.S. Pat. Nos. 4,258,227, 4,266,084 and 4,393,264 which are incorporated into this application and made part hereof. The catalyst components in the aforementioned U.S. patents are converted to forms in the resultant ash which are difficult and/or expensive to convert to reusable forms for the oxidation of the methyl-substituted benzenes. Although, in such residues, the substituted benzene and toluene compounds, whose substituents are the carboxy-, aldehyde- and methylol substituents, are individually desirable and useful commercial products, it is not economically feasible to separate and recover the individual compounds from the residues.

Cobalt and manganese acetates are major components of the catalyst system used for oxidizing p-xylene, m-xylene and pseudocumene. These catalyst metals are present in the oxidation residues produced by the various oxidation processes. The oxidation residues are disposed of by incineration leaving a mixed metal oxide ash. The recovery of cobalt and manganese from this incinerator ash would not only reduce catalyst costs but eliminate any costs associated with disposal of the ash.

Strong mineral acids, such as hydrochloric acid, hydrobromic acid, sulfuric acid and nitric acid will react with the metal in the ash. However, depending on the acid used, halogens, $SO_x$ or $NO_x$ are released into the vent gas and scrubbers must be employed to remove these materials from this stream. Also, special equipment, such as glass-lined vessels and piping, are required to handle these strong mineral acids. Once the cobalt and manganese are reacted, further processing must take place to convert the cobalt and manganese ions into the acetate salts.

In our novel process, acetic acid at elevated temperatures and pressures is used to solubilize the cobalt and manganese in the form of the acetate salts directly. Special glass-lined equipment is not required to handle this processing, and since only $H_2O$ and $CO_x$ are produced as by-products, special scrubbers are not required.

This process is also useful in recovering cobalt and manganese from the char or sand bed from a residue pyrolysis unit. When the oxidation residue is pyrolyzed in a pyrolysis unit, the cobalt and manganese become deposited on the sand bed. This sand bed is then treated with the aliphatic carboxylic acid at elevated temperatures and pressures to recover the cobalt and manganese as carboxylic acid salts. The preferred aliphatic acid is acetic acid.

Our novel process is a process for the nearly quantitative recovery of cobalt and manganese from oxidation residue incinerator ash, pyrolysis char or pyrolysis sand. Oxidation residue from p-xylene, m-xylene or pseudocumene oxidations containing cobalt and manganese catalyst metals can be disposed of by incineration or by other processes disclosed in the aforementioned three United States patents. A mixed metal oxide of cobalt and manganese is produced by the incineration of this residue. A cobalt and manganese aliphatic carboxylic acid solution can be obtained directly from this mixed metal oxide by contacting it with the aliphatic acid at elevated temperatures and pressures. Other processes use strong acids, such as hydrochloric acid, hydrobromic acid, sulfuric acid or nitric acid, to recover the metals from the ash but further processing is required to obtain cobalt and manganese acetate from these strong acid solutions. Our process is also useful in recovering cobalt and manganese from the char or sand bed from a pyrolysis unit. This process is inexpensive as it can be carried out in state-of-the-art oxidation reactors and does not require glass-lined vessels or special effluent gas scrubbers. The preferred aliphatic carboxylic acid is acetic acid.

The residue from p-xylene, m-xylene or pseudocumene oxidations, using cobalt and manganese as part of the catalyst system, is burned in an incinerator producing a cobalt and manganese mixed oxide. The incinerator ash is combined with glacial acetic acid or mixtures of acetic acid and water and heated under pressure in a stirred reactor. The acetic acid used can contain 0 to 50 wt % water but glacial acetic acid is preferred. The ratio of acetic acid to incinerator ash charged to the reactor may vary from 1:1 to 50:1 with 5:1 to 15:1 being the preferred range. The temperature may vary from 120°–300° C. with 200°–250° C. being preferred. The operating pressure depends on the temperature employed for the reaction as it should be sufficient to maintain the acetic acid in the liquid state. Pressures from 3–30 atmospheres are preferred. The time required to obtain a maximum recovery of metal acetates from the ash will also depend on the reaction conditions employed. One to three hours should be sufficient at the preferred conditions to obtain nearly quantitative recoveries of cobalt and manganese. A process for the recovery of cobalt and manganese from solid aromatic acid oxidation incinerator ash, pyrolysis sand and pyrolysis char, which process comprises heating such solid in the presence of acetic acid, wherein the weight ratio of the aliphatic acid, to the solid is about 1:1 to about 50:1, at a temperature of about 120° to about 300° C. and a pressure of about 3 to about 30 atmospheres, and recovering the liquid cobalt and manganese in solution as the metal aliphatic acid salt.

After the reaction is complete, the reactor contents are cooled and then depressurized. Water may be added to the reactor at this time to ensure that all of the recovered metal acetates are solubilized as the solubility of the cobalt and manganese acetates is greater in water than in acetic acid.

The reactor solution is then sent to a filter or centrifuge to remove any unreacted ash particles or refractory material that may have contaminated the ash. This solution can then be recycled to the feed mix drum of the oxidation unit.

If large amounts of corrosion metals such as iron are present in the recovered solutions, the pH of the solution can be adjusted to above 3.0 to cause the iron to precipitate before the solution goes to the centrifuge or filter.

Advantageously, in our process acetic acid is used for the extraction of the cobalt and manganese catalyst instead of a strong mineral acid so that the metal acetates can be sent back to an oxidation reactor and reused as catalyst.

In the preferred process, about 10:1 ratio of glacial acid to pyrolysis sand is mixed in a titanium vessel. The vessel is sealed and the mixture heated to 400° F. for three hours. The liquid containing the metal acetates is separated from the sand. The sand can be washed with water, dried and reused in the pyrolysis furnace. Our process recovers cobalt and manganese from pyrolyzed oxidation residue as a reusable catalyst solution.

Our process can be used to recover cobalt and manganese from oxidation residue incinerator ash, pyrolysis sand or pyrolysis char as a solution of cobalt and manganese acetates. This solution can then be sent to the feed mix vessel of an oxidation unit. This is an inexpensive method of reducing the catalyst costs of the oxidation process and eliminates the ash disposal costs.

The advantages of this process for recovering the cobalt and manganese center around the use of acetic acid at elevated temperatures and pressures. Strong mineral acids will also solubilize the cobalt and manganese as shown in Japanese Pat. No. 104524/78; however, halogens, $SO_x$ or $NO_x$ gases are produced which must be scrubbed from the vent gas. Special expensive corrosion resistant equipment is required to handle these strong acids, and expensive additional processing of the cobalt and manganese solution must be carried out to convert the cobalt and manganese to the acetates. This process only produces $H_2O$ and $CO_x$ by-products, current spare oxidation vessels can be used for the reaction, and the acetate salts of cobalt and manganese are formed directly.

In certain instances, the recovery of cobalt and manganese from residues obtained from the pyrolysis of terephthalic acid bottoms residue can be increased by the use of steam in the pyrolysis reaction. The use of steam promotes the formation of forms of cobalt and manganese which are soluble in hot glacial acetic acid. The metals are recovered as acetates which may be directly recycled as the oxidation catalysts. The high value of cobalt makes recovery of this metal particularly desirable to maximize the economics of the alkylbenzene oxidation processes.

Background information concerning pyrolysis processes for aromatic acid residues is set forth in U.S. Pat. Nos. 4,258,227, 4,266,084 and 4,393,264 which are incorporated in this application and made part hereof.

Studies of the effect of pyrolysis char preparation temperature upon cobalt and manganese extraction properties showed that, in the absence of steam, the cobalt and manganese were converted into relatively insoluble forms at reaction temperatures above about 500° C. We prepared samples of terephthalic acid bottoms residue pyrolysis char in the absence of steam at different reaction temperatures (550°, 600°, 750° C.), and extracted the char samples with glacial acetic acid (acetic acid/char wt. ratio =10/1) at about 90° C. for 15 minutes. It was seen that the char preparation temperatures had a marked effect upon the cobalt and manganese extraction properties. Whereas about 80 wt % of the metals were extracted from char prepared at 500° C., only 20 to 30 wt % of the metals were extracted at the higher reaction temperatures.

In order to convert terephthalic acid bottoms residue into hydrocarbons, it is necessary to use a pyrolysis temperature greater than 500° C. and preferably about 750° C. Although a two-step process can be used, e.g., pyrolysis of the residue at 500° C., followed by decarboxylation of the vapor at 750° C., it is advantageous to perform the process in one step at 750° C.

A typical pyrolysis furnace contains a sand bed which is fluidized with air. During pyrolysis, metal oxides are retained on the sand particles. Since most of the metal oxides are formed from the catalyst metals (manganese and cobalt) required in aromatic hydrocarbon oxidation to di- or tricarboxylic acids, it is economically desirable to recover them for reuse as catalysts.

A strong acid, such as hydrobromic acid (HBr), will react with these metal oxides and will also supply bromine used in the catalyst system. However, the resulting metal salt will contain approximately four times the bromide needed in the process unit. Since our reactors utilize manganese and cobalt acetates in acetic acid, it would be more economical to convert the metal oxides directly to acetates with acetic acid. However, acetic acid is a weak acid and will not normally react with metal oxides. Therefore, we needed a method to force acetic acid to react with the metal oxides and form metal acetates directly. To use heat as a driving force in the reaction usually pyrolysis sand is added to the acetic acid in the weight ratio of about 1:2 to about 1:10. In one process, we used a titanium-clad bomb. The bomb was heated to various temperature levels and for different periods of time. The preferred combination of temperature and time required for reaction occurred at about 350°–500° F. and three hours. The pyrolysis sand sample was black (due mostly to metal oxides and carbon) before extraction with acetic acid and white after extraction. The resulting acetic acid solution was a reddish pink color which is indicative of manganese and cobalt acetates. A portion of the acetic acid extracted solutions were diluted with water and analyzed for metals by atomic absorption (AA) which confirmed the presence of manganese and cobalt. A baseline case was determined for metals on the pyrolysis sand from the average of 18 separate analyses by a different method. The acetic acid extraction method results, from an average of six analyses, were compared to the baseline for efficiency calculations (see Tables 1 and 2). Manganese and cobalt oxides are not soluble in water and therefore would not be detected by AA.

Our process is also usable to extract metals from pyrolysis gas particulates, various plant's residue, and waste material. The process is most useful if the metal acetates are recycled to the oxidation reaction for reuse as a catalyst for the manufacture of aromatic di-, or tricarboxylic acids directly in the plant's operation.

Combinations of cobalt and manganese with a source of bromine became preferred for commercial use and is disclosed in U.S. Pat. No. 2,833,816. However, cobalt is very expensive and also available only from sources outside the United States and from countries which may cut off the supply of this valuable metal. Therefore, there is a great incentive to use the catalyst in the oxidation of di- and trimethylbenzenes with molecular oxygen under liquid phase conditions, usually in an acetic acid solvent, in the presence of the recovered cobalt and manganese wherein the oxidation is conducted at a temperature of about 100° C. to about 250° C.

The following examples illustrate the preferred embodiment of this invention. It will be understood that the examples are for illustrative purposes only and do not purport to be wholly definitive with respect to the conditions or scope of the invention.

stripped from their oxides before reuse as a catalyst in a reactor. These oxides can normally be stripped only with a strong acid, but the resulting metal salts could not be sent to a reactor. However, a procedure has been developed to strip cobalt and manganese from pyrolysis sand and incinerator fly ash with acetic acid. These acetates can then be sent to a reactor. 10,000 g of sample of pyrolysis sand or fly ash obtained as residue from aromatic hydrocarbon oxidation, in the presence of cobalt and manganese catalysts, were placed into a 150-ml, air-tight, titanium-clad bomb, or stainless steel bomb, and 100 ml of glacial acetic acid were added and the bomb was heated in an oven for three hours at:

a. 200° C. for pyrolysis sand
    b. 270° C. for fly ash

The extracts were decanted into 100 ml volumetric flasks and analyzed by atomic absorption. The results are set forth in Tables 1 and 2.

In order to establish baselines, the pyrolysis sand and fly ash were extracted with HBr in glass vessels at 90° C. for one hour. The acetic acid extractions were then compared to these results (See Tables 1 and 2). Since a stainless steel bomb was used for development work, some of the bomb metals were extracted as indicated by their increase in concentration. The average percent recovery from pyrolysis sand was 98.8% for cobalt and 100% for manganese.

The recovery from fly ash was 87.6% for cobalt and 84.1% for manganese. The fly ash sample was not as clean nor as uniform as the pyrolysis sand. Fly ash also contains higher oxidation state oxides which are more difficult to strip. Therefore, the fly ash extraction is less efficient than pyrolysis sand extraction.

TABLE 1

| PYROLYSIS SAND | | | | | | | | | | | |
|---|---|---|---|---|---|---|---|---|---|---|---|
| | Percent | | | | | | | | | | |
| | Mn | Co | Ni | Fe | Cr | Na | K | Cu | Zn | Al | Sand |
| Baseline* | 15.91 | 2.916 | 0.030 | 0.186 | 0.030 | 1.226 | 0.007 | 0.0 | 0.002 | 0.010 | 65.20 |
| Test Number | | | | | | | | | | | |
| 1 | 15.30 | 2.55 | 1.09 | 5.65 | 2.30 | 0.90 | 0.015 | 0.055 | 0.12 | 0.07 | 63.21 |
| 2 | 16.90 | 3.06 | 0.25 | 1.41 | 0.42 | 1.13 | 0.14 | 0.0 | 0.05 | 0.71 | 66.50 |
| 3 | 17.10 | 3.05 | 0.28 | 1.59 | 0.45 | 1.12 | 0.05 | 0.0 | 0.07 | 0.78 | 67.10 |
| 4 | 15.40 | 2.72 | 0.26 | 1.20 | 0.28 | 1.15 | 0.065 | 0.03 | 0.11 | 0.90 | 67.73 |
| 5 | 15.91 | 2.83 | 0.21 | 0.90 | 0.21 | 1.08 | 0.0 | 0.07 | 0.11 | 0.12 | 67.13 |
| 6 | 15.50 | 3.07 | 0.19 | 0.87 | 0.18 | 1.08 | 0.0 | 0.08 | 0.08 | 0.18 | 65.77 |
| Average | 16.02 | 2.88 | 0.38 | 1.94 | 0.64 | 1.08 | 0.05 | 0.04 | 0.09 | 0.46 | 66.24 |
| from Baseline** | +0.11 | −0.036 | +0.35 | +1.754 | +0.61 | −0.146 | +0.043 | +0.04 | +0.088 | +0.45 | +1.04 |
| % Recovery | 100.7 | 98.8 | | | | 88.1 | | | | | |

*The baseline is an average of 18 separate analyses.
**Manganese shows a % recovery above 100% due to sampling and analytical variability. The other metals above 100% recovery were due to extraction from the bomb and analytical variability (concentration too low for accurate analyses).

EXAMPLE 1

During pyrolysis or incineration of oxidation residue, metal oxides are formed. Cobalt and manganese must be

TABLE 2

| FLY ASH | | | | | | | | | | | |
|---|---|---|---|---|---|---|---|---|---|---|---|
| | Percent | | | | | | | | | | |
| | Mn | Co | Ni | Fe | Cr | Na | K | Cu | Zn | Al | Residue |
| Baseline* | 26.45 | 5.07 | 0.06 | 1.26 | 0.06 | 1.00 | 0.06 | 0.0 | 0.06 | 1.42 | 39.0 |
| Test Number | | | | | | | | | | | |
| 1 | 21.00 | 4.28 | 0.05 | 1.59 | 0.75 | 0.61 | 0.0 | 0.01 | 1.03 | 1.18 | 43.0 |
| 2 | 23.50 | 4.60 | 0.28 | 2.18 | 0.52 | 0.88 | 0.02 | 0.003 | 0.22 | 0.18 | 46.8 |
| Average | 22.25 | 4.44 | 0.165 | 1.89 | 0.64 | 0.745 | 0.01 | 0.007 | 0.625 | 0.68 | 44.9 |
| from Baseline** | −4.20 | −0.63 | +0.105 | +0.63 | +0.58 | −0.255 | −0.05 | +0.007 | +0.565 | −0.74 | +5.9 |
| % Recovery*** | 84.1 | 87.6 | | | | 74.5 | | | | | |

*Average of three separate analyses.
**All metals above 100% recovery indicates extraction from the bomb.
***All tests were at 260° C., however, calculations show that a higher recovery would occur at 270° C. The lab oven would not hold temperatures above 260° C.

EXAMPLE 2

To a 500-ml, round-bottom flask, equipped with a reflux condenser and an electrical heating mantle were charged 50 g of p-xylene oxidation incinerator ash, 350 ml of acetic acid and 50 ml of water. The mixture was refluxed for 16 hours causing a slight orange color to appear in the solution. The solids were recovered by filtration, dried and weighed. The weight of these solids was 49.7 g. The extended reflux of the ash in the acetic acid and water at atmospheric pressure was ineffective in recovering cobalt and manganese, as evidenced by the minimal dissolution of the ash.

EXAMPLES 3-6

For each of these examples, 15 g of p-xylene oxidation incinerator ash and 200 ml of acetic acid were charged to a 300 cc Hastalloy C autoclave equipped with a magnadrive stirrer, heater and pressure gauge. The stirrer was operated at 1100 rpm, the pressure was 22 atmospheres, and the temperature was 246° C. After the reaction was ended and the vessel was drained, 100-250 ml of water were used to wash out the reactor. This wash was combined with the vessel drainings and the solution was filtered to remove any unreacted ash or refractory. The solids were dried, weighed and analyzed for cobalt and manganese with x-ray fluorescence. The liquid was weighed and analyzed in the same manner.

The experimental results and recoveries of cobalt and manganese for these examples are reported in Table 3. In all cases, the recoveries of cobalt and mangenese were nearly quantitative, giving recovery values of 98-99 wt %.

TABLE 3
EXPERIMENTAL RESULTS AND RECOVERIES OF COBALT AND MANGANESE

| | Example | | | |
|---|---|---|---|---|
| | 3 | 4 | 5 | 6 |
| Reaction time, hr. | 3 | 4.25 | 5.25 | 6 |
| Solids | | | | |
| Wt., g | 2.27 | 1.86 | 2.45 | 1.02 |
| Co, wt % | 2.13 | 1.16 | 0.72 | 1.79 |
| Mn, wt % | 5.71 | 2.66 | 1.89 | 3.68 |
| Solution | | | | |
| Wt., g | 323.5 | 427.1 | 376.5 | 351.0 |
| Co, wt % | 0.73 | 0.54 | 0.59 | 0.70 |
| Mn, wt % | 1.98 | 1.47 | 1.60 | 1.90 |
| Recovery | | | | |
| Co, wt % | 98 | 99 | 99 | 99 |
| Mn, wt % | 98 | 99 | 99 | 99 |

We claim:

1. A process for the recovery of cobalt and manganese from solid aromatic acid oxidation incinerator ash, pyrolysis sand and pyrolysis char, which process comprises heating such solid in the presence of acetic acid, wherein the weight ratio of the acetic acid to the solid is about 1:1 to about 50:1, at a temperature of about 120° to about 300° C. and a pressure of about 3 to about 30 atmospheres, and recovering the cobalt and manganese in liquid solution as the metal acetic acid salt.

2. A process for the oxidation of di- or trimethylbenzenes with molecular oxygen under liquid phase conditions in the presence of a recovered and recycled cobalt and manganese catalyst, which has been recovered according to the process of claim 1, wherein the oxidation is carried out at a temperature of about 100° C. to about 250° C.

* * * * *

UNITED STATES PATENT OFFICE
CERTIFICATE OF CORRECTION

Patent No. 4,546,202                     Dated  October 8, 1985

Inventor(s) ROBERT C. EDWARDS  -  F. AUSTIN GOLSON

It is certified that error appears in the above-identified patent and that said Letters Patent are hereby corrected as shown below:

Column   Line 3    63    "COx by-products" should be – COx as by-products –

5    50-54  EXAMPLE 1 "During pyrolysis or incineration of oxidation residue, metal oxides are formed. Cobalt and manganese must be"  – should be moved to the top of Column 6 –

Signed and Sealed this

Eleventh  Day of February 1986

[SEAL]

Attest:

DONALD J. QUIGG

Attesting Officer            Commissioner of Patents and Trademarks